US00PP33591P3

(12) United States Plant Patent
Rouwette

(10) Patent No.: US PP33,591 P3
(45) Date of Patent: Nov. 2, 2021

(54) ***LONICERA* PLANT NAMED 'GRLN01'**

(50) Latin Name: *Lonicera nitida*
Varietal Denomination: GRLN01

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 17/135,585

(22) Filed: Dec. 28, 2020

(65) Prior Publication Data

US 2021/0282304 P1 Sep. 9, 2021

(30) Foreign Application Priority Data

Mar. 4, 2020 (QZ) ..... 20200653

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Lonicera* plant named 'GRLN01' that is characterized by its evergreen, winter hardy habit, its very dense, well-branched growth habit that is easy to shape, its foliage that is glossy, fine and green in color, its clean foliage with no disease problems.

2 Drawing Sheets

Botanical classification: *Lonicera nitida.*
Variety denomination: 'GRLN01'.

CROSS-REFERENCE TO A RELATED APPLICATION

This application claims priority to European Community Plant Variety Office (CPVO) Plant Breeder's Rights Application No. 2020/0653 filed on Mar. 4, 2020 under 35 U.S.C. 119(f), the entire contents of which is incorporated by reference herein.

This application is co-pending with a U.S. Plant Patent Applications filed for plants derived from the same breeding program that are entitled *Lonicera* Plant Named 'GRLN02' (U.S. Plant patent application Ser. No. 17/135,656) and *Lonicera* Plant Named 'GRLN03' (U.S. Plant patent application Ser. No. 17/135,656).

BACKGROUND OF THE INVENTION

The present invention relates to a new and distinct cultivar of *Lonicera nitida* and will be referred to hereafter by its cultivar name, 'GRLN01'. 'GRLN01' is a new cultivar of boxleaf honeysuckle, an evergreen shrub grown for use as an ornamental landscape plant.

The new cultivar was derived from a controlled breeding program conducted by the Inventor at his nursery in Valkenburg, The Netherlands. The overall purpose of the breeding program is to make selections of *Lonicera* plants with new leaf colors and dense foliage. 'GRLN01' arose from crosses made in 2014 with *Lonicera nitida* 'Red Tips' (not patented) as the female parent and an unpatented and unnamed proprietary plants of *Lonicera nitida* from the Inventor's breeding program as the male parent. The seeds were pooled for the crosses and therefore the male parent is unknown. 'GRLN01' was selected as a single unique plant in 2015 from amongst the seedlings derived from the above crosses.

Asexual propagation of the new cultivar was first accomplished by the Inventor using softwood stem cuttings in 2015 in Valkenburg, The Netherlands. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRLN01' as a new and distinct cultivar of *Lonicera.*

1. 'GRLN01' exhibits an evergreen, winter hardy habit.
2. 'GRLN01' exhibits a very dense, well-branched growth habit that is easy to shape.
3. 'GRLN01' exhibits foliage that is glossy, fine and green in color.
4. 'GRLN01' exhibits clean foliage with no disease problems.

The parent plant, 'Red Tips', differs from 'GRLN01' in having new shoots that are burgundy in color and less branching with less dense foliage. 'GRLN01' can also be compared to the *Lonicera nitida* cultivar 'Tidy Tips' (not patented), 'GRLN02', and 'GRLN03'. 'Tidy Tips' differs from 'GRLN01' in having a slower growing habit, new shoots that are bronze in color, winter foliage that is red in color, and leaves that are smaller in size. 'GRLN02' differs from 'GRLN01' in having foliage that is dark green in color with new shoots that are purple in color. 'GRLN03' differs from 'GRLN01' in having new foliage shoots that are orange-brown in color.

BRIEF DESCRIPTION OF THE DRAWINGS

The accompanying color photographs illustrates the overall appearance and distinct characteristics of the new *Lonic-*

*era*. The photographs were taken of a 7-month-old plant of the new cultivar as grown outdoors in a 17-cm container in Wernhout, The Netherlands.

Figure 1:
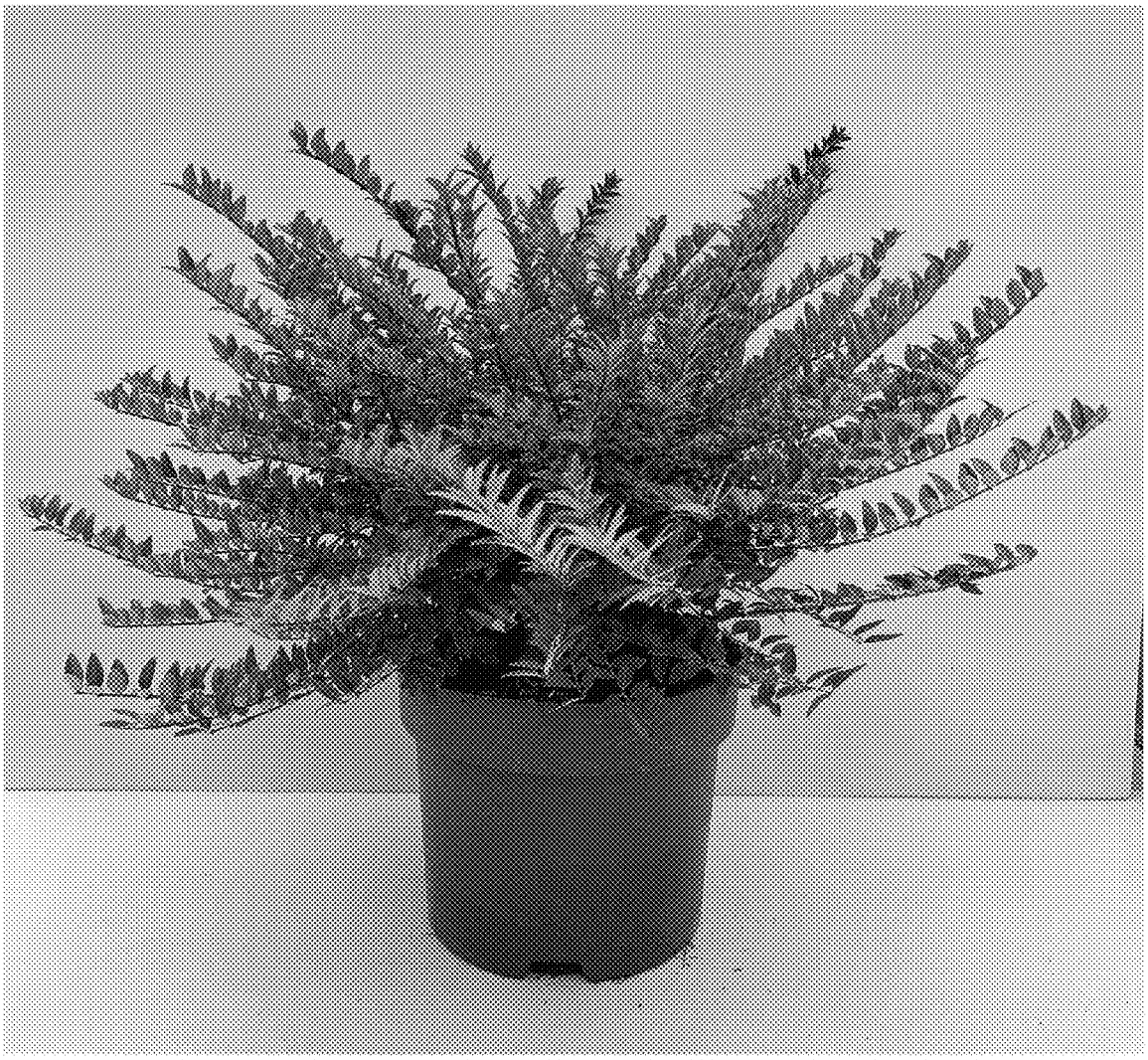

The photograph in FIG. 1 provides a side view of 'GRLN01'.

Figure 2:
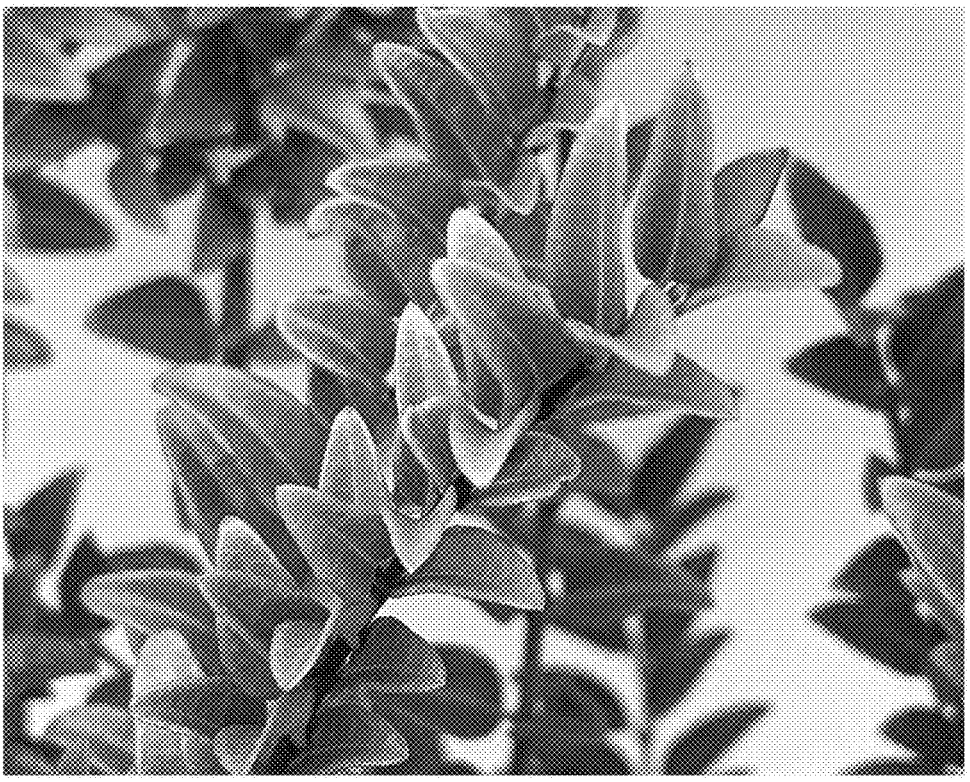

The photograph in FIG. 2 is provides a side view of the branches and foliage of 'GRLN01'.

Figure 3:
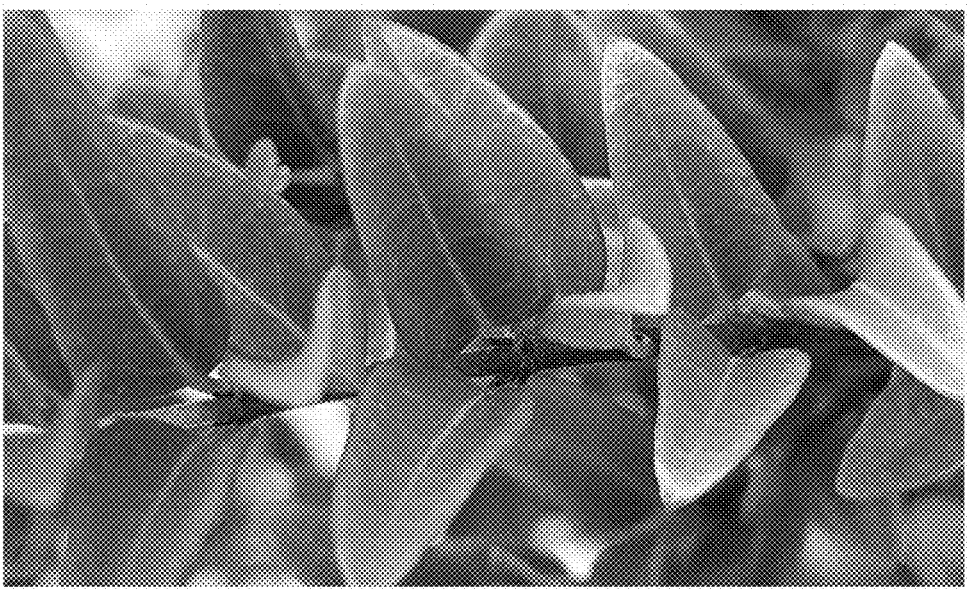

The photograph in FIG. 3 is provides a close-up view of the leaves of 'GRLN01'.

The colors in the photographs are as close as possible with the digital photography and printing techniques utilized and the color codes in the detailed botanical description accurately describe the new *Lonicera*.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantipp (inventor's representative), Plantarium digital expo, Green Leaf, About Plants Zundert, Flor Access, and Nova photo graphic.

DETAILED BOTANICAL DESCRIPTION OF THE PLANT

The following is a detailed description of 7-month-old plants of the new cultivar as grown outdoors in 17-cm containers in Wernhout, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen shrub.

*Plant habit*.—Upright-spreading, well-branched.

*Plant size*.—Average of 24 cm in height and 50 cm in spread as grown in a 17-cm container.

*Cold hardiness*.—At least hardy to U.S.D.A. Zone 6.

*Diseases and pests*.—No susceptibility or resistance to diseases or pests has been identified, however the plants grown have been observed to be disease and pest free.

*Root description*.—Fibrous.

*Propagation*.—Softwood stem cuttings.

*Root development*.—Cuttings initiate roots in about 6 weeks and fully develop as a young rooted plant in 4 to 5 months in a 1.5 liter pot.

*Growth rate*.—Moderately vigorous.

Stem description:

*Shape*.—Rounded.

*Stem color*.—New growth; upper side 152B, fading to 83A, lower side 152B, mature bark; a color between 199A and N199A.

*Stem quantity*.—Average of 3 main branches, each with an average of 18 lateral branches.

*Stem strength*.—Strong.

*Stem size*.—Main; average of 26 cm in length and 3 mm in diameter, lateral branches; 18 cm in length and 2 mm in diameter.

*Stem surface*.—Matte and slightly pubescent.

*Internode length*.—Average of 1 cm.

*Branching*.—Densely branched, lateral branches held at an average angle of 40° to main branches.

Foliage description:

*Leaf shape*.—Ovate.

*Leaf division*.—Simple.

*Leaf base*.—Obtuse to rounded.

*Leaf apex*.—Acute to rounded.

*Leaf fragrance*.—None.

*Leaf venation*.—Pinnate, upper and lower surface color; 145A.

*Leaf margins*.—Entire.

*Leaf arrangement*.—Alternate.

*Leaf attachment*.—Petiolate.

*Leaf surface*.—Glabrous and glossy on both surfaces.

*Leaf size*.—Average of 1.7 cm in length and 7 mm in width.

*Leaf quantity*.—Average of 38 per branch.

*Leaf color*.—Young and mature upper surface; N144A, young and mature lower surface; 145A, fall and winter foliage upper and lower surface; similar to mature foliage.

*Petioles*.—About 1 mm in length and width, 145A in color, glabrous surface.

*Stipules*.—About 0.7 mm in length and width, 199A in color, glabrous surface.

Inflorescence description: Flowers and seed production have not been observed to date.

It is claimed:

1. A new and distinct cultivar of *Lonicera* plant named 'GRLN01' as herein illustrated and described.

* * * * *